United States Patent [19]
Olinger et al.

[11] Patent Number: 5,846,568
[45] Date of Patent: Dec. 8, 1998

[54] DIRECTLY COMPRESSIBLE LACTITOL AND METHOD

[75] Inventors: Philip M. Olinger, Terre Haute, Ind.; Julita Pearson, West Wielihaui, United Kingdom

[73] Assignee: Xyrofin Oy, Kotka, Finland

[21] Appl. No.: 715,825

[22] Filed: Sep. 19, 1996

[51] Int. Cl.⁶ ............... A61K 9/16; A61K 9/20; A61K 47/26
[52] U.S. Cl. ........... 424/499; 424/489; 424/465; 514/952; 514/960
[58] Field of Search ................... 424/469, 465, 424/441, 489, 499; 428/402; 426/658; 514/952, 960

[56] References Cited

U.S. PATENT DOCUMENTS

| | | |
|---|---|---|
| 5,021,249 | 6/1991 | Bunick et al. . |
| 5,204,115 | 4/1993 | Olinger et al. ............ 424/470 |
| 5,322,694 | 6/1994 | Sixsmith . |
| 5,501,861 | 3/1996 | Makino et al. . |
| 5,536,526 | 7/1996 | Virtanen et al. ............ 426/658 |
| 5,576,014 | 11/1996 | Mizumoto et al. . |
| 5,612,053 | 3/1997 | Baichwal et al. . |
| 5,651,988 | 7/1997 | Olinger et al. ............ 424/489 |

OTHER PUBLICATIONS

Derwent Abstract for JP 9216816 A.

*Primary Examiner*—Edward J. Webman
*Attorney, Agent, or Firm*—Baker & McKenzie

[57] ABSTRACT

A directly compressible non-cariogenic free-flowing lactitol granulate comprising milled lactitol and a physiologically acceptable, binder taken from the group consisting of sugar alcohols, polymerized reducing sugars, alkali carboxymethylcellulose, hydrogenated starch hydrolysate, hydroxypropylcellulose, physiologically acceptable cellulose derivatives, polyvinylpyrrolidone, gum arabic, and other physiologically acceptable gums. The granulate is directly compressible, and manifests the taste profile, metabolic, and non-cariogenic properties of lactitol. In one embodiment, the milled lactitol is present in the granulate in the range of about 70% to about 98% by dry weight and the physiologically acceptable, non-cariogenic binder is present in the granulate in the range of about 2% to about 30% by dry weight. In a preferred embodiment of the invention, the granulate consists of 70–98% milled lactitol and 2–30% of a lactitol binder.

13 Claims, No Drawings

DIRECTLY COMPRESSIBLE LACTITOL AND METHOD

I. INTRODUCTION

This invention relates to a directly compressible lactitol granulate. The granulate consists of lactitol and a physiologically acceptable, non-cariogenic binder taken from the group consisting of non-cariogenic sugar alcohols (including lactitol), polydextrose, an alkali carboxymethylcellulose, hydrogenated starch hydrolysate, and combinations thereof. The preferred binder is lactitol. The invention also relates to a method of producing a directly compressible lactitol granulate which can be used in tabletting contexts; the granulate exhibits acceptable flow characteristics and has an appropriate compression profile. The granulate manifests the taste profile, metabolic and non-cariogenic properties of lactitol. The invention also relates to tablets which contain lactitol as a sweetening agent, tablets which exhibit high hardness, low friability, are non-cariogenic and manifest the taste profile and metabolic properties of lactitol.

II. BACKGROUND OF THE INVENTION

A. The Advantages of Lactitol

The most commonly used sweetener for food and pharmaceutical contexts is sucrose. Sucrose is used for its well-known sweetening properties and also for bulking purposes. Although a wide variety of alternate sweeteners are available, sucrose is generally considered to be the optimum sweetener with regard to taste profile and technological properties. However, sucrose has been implicated as a contributory factor in many diseases including hypertension, coronary heart disease, arterial sclerosis and dental caries. These health concerns have led health care professionals to analyze the effects of sucrose and its prominent role in the diet.

Perhaps the most significant, well-documented effect of sucrose is its contribution to tooth decay. The mouth contains a number of bacterial strains which ferment common dietary carbohydrates such as sucrose. This fermentation generates acid as an end product which lowers the pH in the mouth; the lowered pH leads to a demineralization of tooth enamel and finally to the formation of dental lesions or caries.

It is well known that it is not the total quantity of sugar consumed per se, but the frequency of consumption that contributes to dental caries. Thus, the presence of sucrose and other fermentable carbohydrates in regular meals is not the principal cause of tooth decay. The consumption of fermentable carbohydrates between meals in the form of confections and sweetened pharmaceuticals (and the frequency of such consumption) have been shown to have a close relationship to the formation of dental caries. Long after the candy or drug has been consumed, the fermentable carbohydrate stays in the mouth and is fermented by *Streptococcus mutans* and other cariogenic bacteria, lowering the mouth pH and promoting dental caries as described above.

One approach to fighting dental caries is to reduce or eliminate the amount of fermentable carbohydrates such as sucrose in pharmaceutical or food contexts. The replacement of fermentable carbohydrates by sugar substitutes which cannot be fermented, or are less easily fermented by *S. mutans* and other bacteria has been shown to decrease the development of dental caries.

In addition, sucrose requires insulin for its metabolism and as such may not be an acceptable sweetener in the diets of insulin dependent diabetics. A second fermentable carbohydrate is lactose which may be used in tablets. U.S. Pat. No. 5,534,555 to Meygelaars et al. discusses a lactose/lactitol combination mix (not a granulate) which is represented to be "directly compressible". However, the mix is not as free flowing and does not have all of the handling benefits of a granulate, is cariogenic, and does not fully exploit the benefits of lactitol as may be manifested in a tablet context.

Lactitol is a dimeric sugar alcohol which is derived by the catalytic hydrogenation of lactose. Commercially lactitol is available as either a mixture of mono and dihydrates and anhydrous lactitol or as the pure monohydrate and pure anhydrous forms.

The use of lactitol is attractive because of certain taste and technological characteristics which it exhibits. In particular, lactitol has a number of attributes which make it potentially quite useful as a tabletting excipient, including, but not limited to:

1. the pure monohydrate form is essentially non-hygroscopic which enhances its ability to be a stable, free-flowing product which has the potential to provide shelf stable tablets;
2. lactitol offers an aqueous solubility which is similar to sucrose which contributes to its ability to provide a smooth, non-chalky mouthfeel and suitable release of active ingredients;
3. lactitol contributes only 2 kcal/g;
4. lactitol is metabolized independent of insulin requirement and exhibits a glycemic index of essentially zero;
5. lactitol is non-cariogenic; and
6. unlike many sugar alcohols, lactitol exhibits a minimal negative heat of solution (cooling effect) which can interfere with desired flavor systems.

The combination of lactitol's attributes (non-hygroscopicity, solubility, caloric value, metabolic utilization, dental and organoleptic) clearly set lactitol apart from other crystalline sugar alcohols and other alternative bulk sweeteners. For example, while mannitol (a common tabletting excipient) is essentially non-hygroscopic, contributes 1.6 kcal/g, is non-cariogenic and is metabolized independent of insulin, mannitol contributes a noted cooling effect and a low solubility which often results in a chalky mouthfeel. Sorbitol and xylitol contribute noted cooling effects and moderate hygroscopic properties. Maltitol is moderately hygroscopic and exhibits a moderate insulin requirement and 3 kcal/g. Isomalt, like mannitol, exhibits a low solubility which can impact on tablet mouthfeel.

One context in which lactitol has been heretofore utilized with only limited success is as a constituent in tablets. In pharmaceutical contexts, tablets are used for bringing active substances into a size, shape and texture that can be dosaged, chewed, sucked, swallowed whole or dissolved in water for drinking. In food contexts, tablets can take the form of compressed, fruit or mint flavored confections which consist of a sweetener(s), flavor(s) and optionally color and acid. Because of its taste and other properties as described above, lactitol is a potentially attractive constituent in tablets for both food and pharmaceutical purposes. Other polyols have been utilized in tablet contexts as diluents, flavoring agents and binders, but lactitol has not heretofore been used extensively in this context.

B. Tabletting Techniques and Tablets

Tablets can be formed by compression or by molding. Simple compression techniques have been known for centuries; in 1577 Hieronymous Bosch, in his Kreuttenbuch, describes a simple press, used for making medicines. The sugar coating of "pills" was first attributed to Jean de Renou in 1606, and one of the first patents for the manufacture of "pills and medical lozenges" was granted to one Thomas Brockedon in Great Britain in 1843. Many types of tablets exist including chewable tablets, lozenges, effervescent, coated centers, film coated tablets, enteric coated tablets, time release tablets (for release of ingredients over time) multi-layered tablets and others.

Modern compression tabletting techniques—irrespective of the type (and ultimate shape of the end product)—utilize a piston like device with three stages in each cycle: (1) filling—adding the constituents of the tablet to the compression chamber; (2) compression—forming the tablet; and (3) ejection—removing the tablet. The cycle is then repeated. A representative tablet press is a MANESTY EXPRESS 20 rotary press, manufactured by Manesty Machines Ltd., Liverpool, England, and many others are available.

In order to make tablets, preferably all ingredients—or at least the carrier or diluent which typically makes up the bulk of the tablet—must have certain physical characteristics, including the ability to flow freely, and acceptable cohesion (or compressibility). Because many materials have some, or none, of these qualities, techniques must be developed to impart these characteristics to the constituents. In this context, "free flowing" means that the particles to be compressed must enter the compression chamber as discreet particles. While particles which are not "free flowing" can be used in tabletting contexts, they can be utilized only if force feeders or other mechanical means are utilized to move the particles. Such methods add to the expense of the process, and decrease the efficiency considerably; therefore, they are rarely used. "Compressible" means the particles form a tablet after compression and do not remain in a powdered or substantially powdered form.

Two critical criteria in the quality of a tablet are crushing strength (or hardness) and friability. The resistance of the tablet to chipping, abrasion, or breakage under conditions of storage, transportation and handling before usage depends on its hardness. Hardness is measured by determining lateral breaking strength (expressed in kilo pounds or Strong Cobb Units wherein 1 kp=1.4 S.C.U.) exerted on a single tablet at the moment of rupture. A representative hardness tester is the Model HT-300 manufactured by Key International, Inc. Acceptable hardness depends on the desired mouthfeel and the expected end use and packaging conditions of the tablet, but in most contexts, tablet hardness must be greater than about 10 S.C.U. to be commercially useful.

Friability is also a standard test known to one skilled in the art. Friability is measured under standardized conditions by weighing out a certain number of tablets (generally 20 or more), placing them in a rotating plexiglass drum in which they are lifted during replicate revolutions by a radial louver, and then dropped through the diameter of the drum. After replicate revolutions, the tablets are reweighed and the percentage of powder "rubbed off" or broken pieces is calculated. Friability in the range of about 0% to 3% is considered acceptable for most drug and food tablet contexts. Friability which approaches 0% is particularly preferred.

Tablets of insufficient hardness exhibit capping and/or lamination and can easily break apart or disintegrate under normal handling and packaging conditions. Tablets of insufficient hardness cannot be used for lozenges or mints which are designed to be sucked in the mouth, releasing the active ingredient(s) or flavor over time, and may have an undesirable powdery, grainy or coarse mouthfeel.

C. Use of Lactitol in Tablet Contexts

Lactitol is not considered to be directly compressible, i.e. crystalline lactitol cannot be compressed into tablets of sufficient hardness and low friability. Therefore, in order to utilize lactitol in tablets, a variety of approaches to impart these characteristics have been used, without complete success.

When milled lactitol monohydrate having a mean particle size of about 65 microns was tabletted on a Manesty F3 press utilizing 1% magnesium stearate as the lubricant, tablets with acceptable hardness and friability were obtained. However, the coefficient of tablet weight variance was excessive (>4%). The high variance was attributed to the poor flow characteristics of the milled lactitol. The addition of up to about 8% talc to the milled lactitol sufficiently improved product flow and reduced tablet weight variance to an acceptable level at the expense of poor tablet friability (>67%).

When crystalline lactitol monohydrate having a mean particle size of about 500 micron was tabletted on a Manesty F3 press utilizing 1% magnesium stearate as lubricant, acceptable flow characteristics were observed and uniform tablet weights were obtained. However, tablet hardness was marginal at best and tablet friabilities were excessive.

Attempts to combine milled and crystalline lactitol monohydrate in a 1:1 weight ratio resulted in tablets with marginally acceptable hardness, higher than acceptable friability and less than desired flow characteristics and table weight uniformity.

When crystalline anhydrous lactitol of varying mean particle sizes is tabletted, tablets with initially acceptable hardness and friability may be obtained. However, presumably because of anhydrous lactitol's tendency to absorb atmospheric water and move towards the monohydrate form, the tablets become notably softer upon even mild ambient storage conditions.

SUMMARY OF THE INVENTION

The present invention contemplates a directly compressible, non-cariogenic free-flowing lactitol granulate having an average particle size of up to 500 microns. The granulate comprises lactitol and a physiologically acceptable, non-cariogenic binder; acceptable binders include sugar alcohols, polymerized reducing sugars, alkali carboxymethylcellulose, hydrogenated starch hydrolysate, hydroxypropylcellulose, physiologically acceptable cellulose derivatives, PVP, gum arabic and other physiologically acceptable gums. The particularly preferred sugar alcohol binder is lactitol, the particularly preferred polymerized reducing sugar binder is polydextrose, and the particularly preferred alkali carboxymethylcellulose binder is sodium carboxymethylcellulose. The granulate can also include an intense sweetener.

A further embodiment of the invention includes a directly compressible, non-cariogenic, free-flowing lactitol granulate, which comprises milled lactitol with a lactitol binder. The binder is present in the granulate at levels of between about 2% to about 30% by weight, with levels of 5% to 15% being preferred, and levels of 10% to about 15% being particularly preferred.

The invention also contemplates a relatively stable, non-cariogenic consumable tablet, formed by direct compression means comprising lactitol, and a physiologically acceptable, non-cariogenic binder. The tablet may also include other excipients, including microcrystalline cellulose, physiologically acceptable cellulose derivatives, starch, food grade starch derivatives, and non-cariogenic sugar alcohols. The tablet may also include intense sweeteners.

The present invention also contemplates a method for the production of a directly compressible, free-flowing, non-cariogenic lactitol granulate which consists of granulating milled lactitol with a mean particle size of less than about 300 microns with a physiologically acceptable, non-cariogenic binder. The binders include those mentioned above, with a particularly preferred binder being lactitol. In a preferred embodiment, the lactitol is utilized in an aqueous solution in concentration of between about 30% to about 60% by weight, with concentrations of between about 45% to about 55% being particularly preferred.

BRIEF DESCRIPTION OF THE DRAWINGS

FIG. 1 shows the stability of tablets made from a lactitol granulate compared to tablets made from a commercially available tabletting grade mannitol.

FIG. 2 shows the results of compression studies comparing the hardness of tablets made from a lactitol granulate of the present invention, tablets made from a commercially available tabletting grade mannitol, and lactose.

DETAILED DESCRIPTION OF THE PREFERRED EMBODIMENT

A. General

The granulate of the present invention exhibits excellent flowability and compressibility when used in typical tabletting equipment, such as a Manesty Express 20 rotary tabletting press or other tabletting presses which are known to one of ordinary skill in the art. The lactitol used to form the granulate is lactitol milled to an average particle size of less than about 300 microns, preferably with a mean size of between about 30–200 microns, with a mean size of between about 50 to about 90 microns being particularly preferred. Crystalline lactitol can be milled, ground or otherwise comminuted to reach the preferred particle size.

The binder contemplated by the present invention is a physiologically acceptable, non-cariogenic binder. Surprisingly and unexpectedly, an aqueous lactitol solution functions as an excellent binder in this context. Lactitol is not known as a binder and is not generally used as such. However, an aqueous lactitol solution of between about 30%–60% (by weight) has been found to work extremely well as a binder in the present invention. An aqueous solution of lactitol of between about 45 %–55% (by weight) is preferred, with a solution of between about 49%–51% (by weight) particularly preferred. The resulting granulate is thus comprised solely of lactitol, thereby allowing full expression of all of its taste and technological benefits.

Other acceptable binders include polydextrose. Polydextrose is available from Cultor Food Science, New York, N.Y. Polydextrose is a water-soluble, randomly bonded condensation polymer of dextrose, containing minor amounts of bound sorbitol and an acid catalyst. Polydextrose is available in a number of different forms. Other physiologically acceptable, non-cariogenic polymers of reducing sugars may also function as binders in this context.

Another binder is an alkali carboxymethylcellulose such as sodium carboxymethylcellulose. Sodium carboxymethylcellulose can be utilized in a wide range of cosmetic, food, pharmaceutical and industrial applications, but has heretofore not been utilized as a binder with lactitol in tabletting contexts. Sodium carboxymethylcellulose is available from Aqualon Company, Wilmington, Delaware. Sodium carboxymethylcellulose is a cellulose ether produced by reacting alkali cellulose with sodium monochloroacetate under controlled conditions. Sodium carboxymethylcellulose is available in food, pharmaceutical and standard grades with varying degrees of substitution (from 0.38 to 1.4) and viscosity characteristics in solution with water.

A further binder is hydrogenated starch hydrolysate. Hydrogenated starch hydrolysate is the catalytically hydrogenated product of high maltose syrup and is commercially available from a wide variety of sources. Other functional binders can include hydroxypropylcellulose, other physiologically acceptable cellulose derivatives, PVP, gum arabic and other physiologically acceptable gums.

The level of lactitol binder in the final dried product (as a percentage of dry weight) will be between about 2% to about 30%, with a preferred percentage of between about 5% to about 15%, with a percentage of about 10% to about 15% being particularly preferred.

Granulation of the lactitol and binder can be achieved with any of the standard means of granulation available. Suitable commercial granulators or granulating systems include the Lodige horizontal blender (Gebruder Lodige GmbH) in combination with a fluidized bed dryer, the Glatt vertical fluidized bed granulator (Glatt GmbH, Binzen, West Germany), the Aeromatic vertical fluidized bed granulator (Aeromatic AG, Bubendorf, Switzerland) and the Schugi granulator (Schugi, BV, Lelystad, Holland). Other granulation devises commonly known to those skilled in the art can be utilized in the practice of our invention.

The produced and dried granulate is usually screened following the granulation step to remove coarse particles. A suitable sieve size for this purpose is a 16 mesh (1.2 mm) screen. The coarse particles can either be reworked, milled or dissolved for further use.

The granulate can be utilized as a sweetening, flavor or bulking agent and/or as a diluent in food and pharmaceutical contexts alone, or in combination with other sweeteners (such as intense sweeteners), other polyols and/or other binding agents.

The granulate of the present invention can be used as an excipient in a tablet, alone or in combination with other excipients, lubricant(s), flavoring agents, and/or diluents. The concentration range of the granulate can be from about 5% to about 99.5% by dry weight; other excipients include microcrystalline cellulose, various cellulose derivatives, starch, various starch derivatives, and non-cariogenic sugar alcohols.

B. EXPERIMENTAL

Example 1

Utilizing a SWG15 Glatt Fluid Bed Granulator equipped with a screen at the bottom of the bowl and an exiting granulation comill (Quadro Comil, Model 197-1-064 with a size 2A-.04R031/37 screen, approximately 65 micron milled lactitol monohydrate was granulated with the aid of a 50% (w/w) lactitol monohydrate binder which was prepared and maintained under ambient conditions. Three granulated lactitol products were prepared: A) 6% binder (dry weight basis, dwb); B) 12% binder (dwb); and C) 18% binder (dwb). The conditions of manufacture were as follows: inlet temperature (about 80C); atomizing air pressure (about 5 bar); binder spray rate (about 110 ml/min); and outlet air temperature (about 34C during the processing cycle and about 44C at the end of drying cycle). Products B and C were produced with an air flow of about 200 cfm while product A was produced with an air flow of about 250 cfm. Each product exhibited satisfactory flow properties, moisture levels of about 4.6%, loose bulk densities of about 0.58 g/ml, and tapped densities of about 0.68 g/ml. Approximately 550 mg, 7/16 inch flat faced beveled edge tablets were prepared utilizing each granulated product at 2.0 tons compression force at a rate of 1000 tablets/minute utilizing a Manesty Express 20 rotary tabletting press. Each product yielded pleasant tasting tablets which exhibited excellent hardness and acceptable friability. The hardness of tablets from the respective products were as follows: A (about 33 Strong Cobb Units, scu); B (about 34 scu); and C (about 22 scu).

Example 2

Lactitol granulate from Example 1B and a commercial granular mannitol were compressed into 15 mm flat faced beveled edge tablets of similar hardness (~20 scu) using 1 % magnesium stearate as the lubricants The tablets were stored over a 23 day period at about 20C and about 75% relative humidity. Moisture increase was monitored. As illustrated by FIG. 1, the lactitol tablets exhibited a moisture increase of only about 0.1 % while the commercial mannitol product exhibited a moisture increase of about 1.0%.

Example 3

The lactitol granulates from Example.s 1A-C exhibited means particle sizes which were below about 200 microns. In an effort to increase the mean particle size of the lactitol granulate, milled lactitol monohydrate was granulated with a 50% (w/w) ambient lactitol solution using the equipment of Example 1 under the following conditions: air flow (250 cfm); inlet temperature (about 85C); atomizing air pressure (about 2.5 bar); spray rate (about 250 ml/min); spray time (about 11 minutes); and outlet temperature (about 38C during the processing cycle and about 45C during the drying cycle). The binder level of the final granulate was about 12% on a dry weight basis. The resulting granulate exhibited excellent flow properties and was essentially dust free. The mean particle size was about 390 micron. Other granulate attributes were as follows: moisture (about 4%); loose bulk density (about 0.45 g/ml); tapped bulk density (about 0.54 g/ml).

moisture level of about 5 %, a loose bulk density of about 0.55 g/ml and a tapped density of about 0.64 g/ml. The granulate was subjected to various comparative evaluations versus both a commercial directly compressible mannitol and a commercial directly compressible lactose. The comparative evaluations included 1) compression profiles; 2) preparation of ascorbic acid (vitamin C) tablets; and 3) assessment of excipient dilution potential utilizing non-granular acetaminophen (APAP) powder as the diluent.

The compression profiles were conducted on 7/16 inch flat faced beveled edge tablets having a mean weight of about 600 mg. Magnesium stearate was utilized at a 0.5% level as the tabletting lubricant. Tablets were prepared on a Manesty Express 20 rotary press. The results of the compression studies, which are illustrated in FIG. 11, suggest that the lactitol granulate performs in a manner which is superior or similar to the two comparative commercial excipients.

The approximate 600 mg tablets containing ascorbic acid were prepared as above utilizing 10% (w/w) ascorbic acid, 87.5% excipient, 2.0% Ac-di-sol and 0.5% magnesium stearate. A compression force of 1.3 tons was utilized. Each excipient produced acceptable tablets as illustrated in Table I.

TABLE 1

| | Ascorbic Acid Tablet Characteristics | | |
|---|---|---|---|
| Property | Lactitol | Mannitol | Lactose |
| Hardness, Kp | 8.4–16.8 | 5.7–11.5 | 9.4–16.0 |
| Thickness, mm | 4.65–4.72 | 4.82–4.90 | 4.87–4.92 |
| Weight Variance, n = 10 | | | |
| Mean, mg | 605 | 605 | 605 |
| Std. Dev. | 4.09 | 3.94 | 3.05 |
| RSD, % | 0.74 | 0.65 | 0.51 |
| Friability, % | 0.82 | 0.74 | 0.24 |

Each excipient was evaluated for dilution potential in conjunction with either 10% or 30% APAP as diluent. Magnesium stearate was utilized as lubricant at the 0.5% level. Tablets were prepared as above utilizing compression forces in the range of 1.3–2.0 tons. Each excipient exhibited similar dilution potentials as illustrated in Table II.

TABLE II

| | Dilution Potential Characteristics | | | | | |
|---|---|---|---|---|---|---|
| | Lactitol | | Mannitol | | Lactose | |
| Property | 10%APAP | 30%APAP | 10%APAP | 30%APAP | 10%APAP | 30%APAP |
| Hardness, Kp | 6.5–11.7 | 2.9–4.2 | 6.6–12.5 | 3.6–5.4 | 6.4–15.4 | 4.4–9.9 |
| Thickness, mm | 4.78–4.90 | 4.74–4.89 | 4.95–5.02 | 5.12–5.19 | 4.59–4.65 | 4.98–5.11 |
| Weight Variance, n = 10 | | | | | | |
| Mean, mg | 597 | 591 | 606 | 601 | 604 | 596 |
| Std. Dev. | 6.6 | 11.0 | 6.4 | 5.9 | 6.5 | 14.0 |
| RSD, % | 1.1 | 1.9 | 0.8 | 1.0 | 1.5 | 2.9 |
| Friability, % | 3.4 | 11.0 | 3.1 | 12.7 | 1.1 | 7.1 |

Example 4

A further granulate was prepared as in Example 3. The resulting granulate had a mean particle size of about 300 micron. The granulate exhibited excellent flow properties, a Example 5

The lactitol granulate was produced on a plant scale utilizing a WSG500 Glatt Fluid Bed Granulator equipped with a 16 micron wire mesh at the bottom of the bowl. The granulate was milled through a Quadro Comil installed on the granulator with a 0.075H37/60 screen size. Milled lactitol monohydrate (with an average particle size of about 65 micron) was bound with 12% dry weight basis ambient lactitol solution (50% w/w). General granulation conditions were as follows: air flow (initial about 2600 cfm, final about 2800 cfm); inlet air temperature (about 85°–90° C.) outlet air temperature (about 30°–33° C.); spray rate (about 3 liters/min); and final cooling temperature (about 29° C). The granulate had a mean particle size of about 280 microns and exhibited excellent blow properties while being essential dust free. The moisture level of the granulate was about 5%. The loose and tapped bulk densities were about 0.57 g/ml and 0/65 g/ml respectively. When compressed on a Manesty Express 20 rotary press to form 600 mg flat faced beveled edge tablets 7/16 inch in diameter at about 1.5 tons compression force using 0.5% magnesium stearate as lubricant, the resulting tablets exhibited a pleasing taste and mouthfeel with no aftertaste. Tablet hardness was about 25 kilopounds (Kp), tablet weight variation was about 1% RSD and tablet friability was less than 1%.

The foregoing general discussion and experimental examples are intended to be illustrative of the present invention, and are not to be considered limiting. Other variations within the spirit and scope of this invention are possible, and will present themselves to those skilled in the art.

We claim:

1. A directly compressible, non-cariogenic free-flowing lactitol granulate having an average particle size of up to 500 microns which comprises: milled lactitol, the milled lactitol being present in the granulate in the range of about 70% to about 98% by dry weight; and a physiologically acceptable, non-cariogenic binder for binding together the milled lactitol, the binder being present in the granulate in the range of about 2% to about 30% by dry weight and the binder being taken from the group consisting of sugar alcohols.

2. The directly compressible granulate of claim 1 wherein said sugar alcohol is lactitol.

3. The directly compressible granulate of claim 1 which additionally includes an intense sweetener.

4. The directly compressible granulate of claim 3 wherein said intense sweetener is taken from the group consisting of dipeptide sweeteners, saccharin, acesulfame K, stevioside, cyclamate, sucralose and neohesperidin dihydrochalcone.

5. A directly compressible, non-cariogenic, free-flowing lactitol granulate having an average particle size of up to 500 microns consisting essentially of: milled lactitol, the milled lactitol being present in the granulate at levels of between about 70% to about 98% by dry weight; and a lactitol binder for binding together the milled lactitol wherein said binder is present in the granulate at levels of between about 2% to about 30% by dry weight.

6. The directly compressible, non-cariogenic, free-flowing lactitol granulate of claim 5 wherein said binder is present in the granulate at levels of between about 5% to about 15% by dry weight.

7. The directly compressible, non-cariogenic, free-flowing lactitol granulate of claim 1 wherein said binder is present in the granulate at levels of 10% to about 15% by dry weight.

8. The directly compressible granulate of claim 1 wherein the milled lactitol has a mean particle size of less than about 300 microns.

9. The directly compressible granulate of claim 5 wherein the milled lactitol has a mean particle size of less than about 300 microns.

10. A directly compressible, non-cariogenic, free-flowing lactitol granulate having an average particle size of up to 500 microns consisting essentially of:

milled lactitol, the milled lactitol being present in the granulate in the range of about 70% to about 98% by dry weight; and a physiologically acceptable, non-cariogenic binder for binding together the milled lactitol, the binder being present in the granulate in the range of about 2% to about 30% by dry weight and the binder being taken from the group consisting of sugar alcohols.

11. The directly compressible granulate of claim 10 wherein said sugar alcohol is lactitol.

12. The directly compressible, non-cariogenic, free-flowing lactitol granulate of claim 11 wherein the lactitol binder is present in the granulate in the range of about 5% to about 15% by dry weight.

13. The directly compressible, non-cariogenic, free-flowing lactitol granulate of claim 12 wherein the lactitol binder is present in the granulate in the range of about 10% to about 15% by dry weight.

* * * * *